United States Patent [19]

Tso et al.

[11] Patent Number: 5,183,931
[45] Date of Patent: Feb. 2, 1993

[54] BENZYLIC OXIDATION AND CATALYST THEREFOR

[75] Inventors: Chung C. Tso; Robert L. Wynn, both of Bartlesville, Okla.

[73] Assignee: Phillips Petroleum Company, Bartlesville, Okla.

[21] Appl. No.: 833,260

[22] Filed: Feb. 10, 1992

[51] Int. Cl.$^5$ .................. C07C 67/00; C07C 51/16; C07C 45/00; C07C 33/18
[52] U.S. Cl. .................. 560/241; 562/412; 562/416; 568/431; 568/435; 568/437
[58] Field of Search .............. 560/241; 562/412, 416; 568/431, 435, 437, 715

[56] References Cited

U.S. PATENT DOCUMENTS 3,547,982 12/1970 McKeon et al. .................. 560/241

OTHER PUBLICATIONS

J. Org. Chem. 33:4123 (1968), Bryant et al.
Synthesis, Jun. 1980, Belli et al.
J. Org. Chem. 34:1106 (1969), Bryant et al.

Primary Examiner—José G. Dees
Assistant Examiner—Joseph M. Conrad, III
Attorney, Agent, or Firm—Lucas K. Shay

[57] ABSTRACT

Oxidation of alkylaromatics having a benzylic hydrogen atom is catalyzed by a catalyst comprising a palladium salt, a metal persulfate, a third metal salt, and a tin salt in a carboxylic acid for a period of time sufficient to convert the alkylaromatics to their corresponding oxidized derivatives. The catalyst is prepared by preheating the palladium salt and the metal persulfate at a temperature sufficient to provide the desired catalytic activity followed by additon of the third metal salt and the tin salt.

14 Claims, No Drawings

BENZYLIC OXIDATION AND CATALYST THEREFOR

FIELD OF THE INVENTION

The invention relates to a catalyst useful for the oxidation of alkylaromatics having a benzylic hydrogen, to a process for preparing the catalyst, and to a process for oxidizing the benzylic hydrogen of the alkylaromatics.

BACKGROUND OF THE INVENTION

Alkylaromatics having a benzylic hydrogen, depending on the oxidizing agents used, can be converted to corresponding carboxylic acids, aldehydes, alcohols, or esters. These products have a variety of uses as intermediates for pharmaceuticals, fragrances, and agricultural chemicals, as plasticizers, and as monomers.

A variety of catalysts have been shown to catalytically convert the alkylaromatics to these corresponding products by oxidizing of the benzylic hydrogen. For example, J. Org. Chem. 33:4123–4127 (1968), discloses that benzyl acetates can be synthesized from the corresponding methylbenzenes by reaction of the methylbenzenes with acetic acid and molecular oxygen catalyzed by a catalyst system comprising a palladium salt, an alkali metal carboxylate, and stannous acetate in acetic acid.

However, the process disclosed in the reference has a very low reaction rate requiring very long reaction time to achieve up to 80% conversion of the methylbenzenes.

SUMMARY OF THE INVENTION

It is therefore an object of the present invention to provide a novel catalyst capable of catalytically oxidizing alkylaromatics, in high conversion and high reaction rates, to the desired corresponding oxidized products.

It is also an object of the invention to provide a process for the preparation of the high activity catalyst.

It is a further object of the invention to provide a process for the catalytic oxidation of the benzylic hydrogen of alkylaromatics employing the high activity catalyst.

According to the present invention, a catalyst useful for oxidizing an alkylaromatic having a benzylic hydrogen to its corresponding oxidized products comprises a palladium salt, a metal persulfate, a third metal salt and a tin salt, in a carboxylic acid.

According to another embodiment of the invention, a process for preparing the catalyst useful for oxidizing an alkylaromatic having a benzylic hydrogen to its corresponding oxidized products comprises: (1) mixing a palladium salt and a metal persulfate, in a carboxylic acid to form a suspension; (2) heating the suspension; and (3) adding a third metal salt and a tin salt to the heated suspension.

According to yet another embodiment of the invention, a process for oxidizing an alkylaromatic having a benzylic hydrogen to its corresponding oxidized products comprises contacting the alkylaromatic in the presence of an oxygen-containing fluid such as air in a reaction medium containing a catalyst comprising a palladium salt, a metal persulfate, a third metal salt and a tin salt, in a carboxylic acid under conditions sufficient to oxidize the benzylic hydrogen of the alkylaromatic.

DETAILED DESCRIPTION OF THE INVENTION

In an embodiment of the present invention, a catalyst useful for oxidation of alkylbenzenes having a benzyl hydrogen comprises a palladium salt, a metal persulfate, a third metal salt and a tin salt, in a carboxylic acid.

The alkylaromatics useful in the present invention have a general formula of

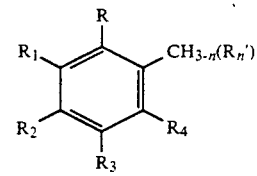

wherein R, $R_1$, $R_2$, $R_3$, and $R_4$ can be each independently hydrogen atoms, the same or different alkyl, alkoxy, or cycloalkyl, groups having 1 to 10 carbon atoms; R' is a saturated alkyl group having 1 to 9 carbon atoms; and n is 0, 1, or 2. Illustrative examples of suitable alkylaromatics are toluene, xylenes, p-tert-butyl toluene, p-octoxy toluene, p-cresol, p-cyclohexyl toluene, and other alkylaromatics.

The palladium salt is a palladium compound which can be partially soluble in the carboxylic acid used in preparing the catalyst or become partially soluble in the carboxylic acid upon reaction with other catalyst constituents. Additionally, the palladium can have an oxidation state of 2, or of 4 that can be reduced to 2 during the course of the reaction, or of 0 that can be oxidized to 2 during reaction.

Exemplary of suitable palladium salts include palladium acrylate, palladium acetate, palladium propionate, palladium nitrate, palladium butyrate, palladium hexansate, palladium cyclohexanoate, palladium chloride, palladium nitrite, and other palladium salts. The preferred is palladium acetate.

The metal persulfate can be partially soluble, or become partially soluble upon reaction with other catalyst components in the carboxylic acid and is selected from the group consisting of lithium persulfate, sodium persulfate, potassium persulfate, maganesium persulfate, and calcium persulfate, and mixtures thereof. Preferred is potassium persulfate.

The third metal salt useful as a component of the catalyst can be partially soluble, or become partially soluble upon reaction with other catalyst components, in the carboxylic acid and has a general formula of MX wherein M is an alkali or alkaline earth metal and X is selected from the group consisting of carboxylate, acrylate, sulfate, nitrate, phosphate, and halide. Illustrative examples of suitable metal salts are lithium acetate, potassium propionate, potassium butyrate sodium acetate, potassium acetate, potassium acrylate, potassium sulfate, potassium phosphate, and potassium chloride, and other metal salts. The preferred is potassium acetate.

The tin salt is a tin compound which can be partially soluble in the carboxylic acid or become partially soluble in the carboxylic acid during the course of reaction with other components of the catalyst. It has an oxidation state of 2, or of 4 that can be reduced to 2, or 0 that can be oxidized to 2 during the course of reaction. Examples of suitable tin salts are stannous acetate, stannous propionate, stannous futyrate, stannous laurate, stannous oleate, stannous benzoate, stannous gluconate, stannous naphthenate, stannous chloride, stannous nitrate, and the like. The preferred is stannous acetate.

The carboxylic acid used in the invention is a non-substituted or substituted aromatic, or saturated aliphatic monocarboxylic or dicarboxylic acid having 1 to 18 carbon atoms. The preferred are saturated aliphatic carboxylic acids. Examples of suitable carboxylic acid include formic acid, acetic acid, propionic acid, butyric acid, octanoic acid, lauric acid, stearic acid, chloroacetic acid, benzoic acid, phenylacetic acid, cyclohexanoic acid, phthalic acid, and the like. Preferred are acetic acid and propionic acid.

The molar ratio of the metal persulfate to the palladium salt ranges from about 1 to about 25, preferably from about 5 to about 20, and most preferably from 8 to 16. The molar ratio of the third metal salt to the palladium salt can be from about 10 to about 100, preferably from about 20 to about 80, and most preferably from 25 to 52. The suitable molar ratio of the tin salt to the palladium salt is from about 0.5 to 10, preferably from about 1 to about 7, and most preferably from 3 to 5. The molar ratio of the palladium salt to the carboxylic acid is about 0.0005 to about 0.005, preferably 0.001 to 0.003.

It is highly desirable to employ an antiagglomerant during the reaction in order to prevent any possible deposition or agglomeration of palladium metal especially on the walls of the reaction system or surfaces of other reaction equipment. Examples of antiagglomerants are charcoal, the many forms of the aluminas, the silicates, silica, etc., which are available commercially and which posses relatively high surface areas, e.g., about several square meter per gram and oftentimes as high as 100 square meters per gram and most preferably even higher than 100 square meters per gram of antiagglomerant. The presently preferred antiagglomerant is charcoal.

The amount of antiagglomerant is not critical. One could employ a weight ratio of antiagglomerant to catalyst of from about 10:1, and lower, to about 1000:1, and higher, on a weight basis.

In another embodiment of the invention, a process for preparing the catalyst is provided which comprises: (1) mixing a palladium salt, a metal persulfate and a third metal salt, in a carboxylic acid, to form a suspension; (2) heating the suspension; and (3) adding additional amounts of the third metal salt and a tin salt to the heated suspension.

The scope of palladium salt, metal persulfate, the third metal salt, tin salt and carboxylic acid is the same as described above.

In a suitable container, such as a flask, that can be equipped with a heater, an agitation means such as a power stirrer, and an addition means such as addition funnel, the palladium salt, the metal persulfate, the third metal salt, and the carboxylic acid can be mixed together.

The molar ratio of the palladium salt to the carboxylic acid is about 0.0005 to about 0.005, preferably 0.001 to 0.003. The molar ratio of the metal persulfate to the carboxylic acid is about 0.01 to about 0.03, preferably 0.02 to 0.025 for maximum catalytic activity. The molar ratio of the third metal salt to the carboxylic acid is about 0.01 to about 0.5, preferably 0.05 to 0.2.

Following a thorough mixing, the salts forms a mixture in the carboxylic acid. Heating is then initiated to and held at about 60° C. to about 150° C., preferably 90° C. to 120° C., for about 5 minutes to about 3 hours, preferably 20 minutes to 1 hour. Although the heating can be done at any pressure, it is preferably carried out at atmospheric pressure.

An extra amount of the third metal salt and the tin salt are then added to the heated suspension with proper mixing. It can be added to the heated suspension which is still hot or has been cooled to any temperature. The molar ratio of the third metal salt to the carboxylic acid is this extra amount is about 0.01 to about 0.5, preferably 0.05 to 0.2. The molar ratio of the tin salt to the carboxylic acid is about 0.001 to about 0.05, preferably 0.005 to 0.01 for maximum catalytic activity. The suspension can be further heated if it is desirable. It can also be mixed for an additional period of time to ensure that all of the third metal salt and the tin salt are well mixed in the suspension.

It is also highly desirable to employ an antiagglomerant during the reaction in order to prevent any possible deposition or agglomeration of palladium metal especially on the walls of the reaction system or surfaces of other reaction equipment. Examples of antiagglomerants are charcoal, the many forms of the aluminas, the silicates, silica, etc., which are available commercially and which possess relatively high surface areas, e.g., about several square meter per gram and oftentimes as high as 100 square meters per gram and most preferably even higher than 100 square meters per gram of antiagglomerant. The presently preferred antiagglomerant is charcoal.

The amount of antiagglomerant is not critical. One could employ a weight ratio of antiagglomerant to catalyst of from about 10:1, and lower, to about 1000:1, and higher, on a weight basis.

The antiagglomerant can be added any time during the preparation of the catalyst system. However, it is highly desirable to add the antiagglomerant in the beginning with the palladium salt to increase the surface area.

According to yet another embodiment of the invention, the novel catalyst prepared by the novel procedure described above is used to catalytically oxidize the alkylaromatics to corresponding oxidized products under conditions sufficient to oxidize the benzylic hydrogen of the alkylaromatics.

The alkylaromatics useful in the present invention are the same as those described above.

The oxidized products of the alkylaromatics can be carboxylic acids, aldehydes, alcohols, or esters. Illustrative products include: benzylacetate, benzylaldehyde, benzylbutyrate, benzylbenzoate, benzylidene diacetate, phenyl alcohol, propyl benzyl ether, tert-butyl benzylacetate, and other corresponding oxidized products.

The molar ratio of the alkylaromatic to the palladium salt can be varied from about 1 to about 100, preferably about 5 to about 50, and most preferably 10 to 30. Generally, the molar ratio can be dependent on the reaction conditions.

The benzylic oxidation of the invention can be conducted over a wide range of temperatures and pressures sufficient to oxidize the benzylic hydrogen, generally depending on the nature of the alkylaromatics, the nature of the carboxylic acid, and the concentration of the reactants. Generally, the reaction can be carried out at as low as 20° C. and at as high as 200° C. A suitable temperature range is from about 40° C. to about 150° C., preferably from 70° C. to 120° C.

Broadly, the benzylic oxidation can be carried out at atmospheric pressure, or at as high as 400 atmospheres.

A suitable pressure range is about 1 atm to about 300 atm, preferably 1 atm to about 100 atm.

The benzylic oxidation of alkylaromatics is conducted for a period of time sufficient to oxidize the benzylic hydrogen to the desired functional groups. The oxidation can be carried out from about 1 minute to about 20 hours, preferably about 5 minutes to about 10 hours, and most preferably 10 minutes to 2 hours not only for complete oxidation of the benzylic hydrogen but also for economic reasons.

The benzylic oxidation can be carried out in a carboxylic acid and, optionally, in the presence of a solvent which is inert to the reactants and products but is capable of increasing the solubility of the reaction mixture. Illustrative inert solvents are N-methylformamide, N,N'-dimethylacetamide, N-methyl-2-pyrrolidone, acetonitrile, propionitrile, diethyl carbonate, and other inert solvent.

The following examples are provided to further illustrate the practice of the present invention.

EXAMPLE I

This example illustrates the reference catalyst and its catalytic activity for oxidizing the benzylic hydrogen of an alkylaromatic to its corresponding ester.

The experiment was carried out in a flask containing a suspension of 0.367 moles of potassium acetate in 2.667 moles of acetic acid and 12 g charcoal with air being blown through the flask at a rate of 500 ml/min. A mixture of palladium acetate (0.005 moles) and stannous acetate (0.021 moles) was then added to the flask to form a catalyst suspension. p-Tert-butyl toluene (0.101 moles) was subsequently added to the catalyst suspension. The reaction mixture was then heated at 100° C. for a period of time indicated in Table 1. An aliquot (1 ml) of the reaction mixture was withdrawn for analysis with a liquid chromatography. The sample was diluted to 10 ml with a premixed solvent comprising 75 volume % acetonitrile and 25 volume % $H_2O$ followed by filtration to remove insolubles. One milliliter of the filtrate was further diluted to 100 ml with the same solvent. The diluted sample (1 ml) was injected into the liquid chromatograph employing a 5C1810μ column (5 mm I.D.; C18 carbon/silica regular/10 micron particles). The results are shown in Table 1 below.

TABLE 1

| | Oxidation of p-Tert-butyltoluene Catalyzed by Pd(OAc)$_2$/SN(OAc)$_2$/KOAc | | | |
|---|---|---|---|---|
| Run | Reaction Time (h) | Conversion (%) | Product | % of Product in Product Mixture |
| 1 | 1 | 3 | p-t-butyl benzylacetate | 3 |
| 2 | 2 | 10 | p-t-butyl benzylacetate | 10 |

The results of Table 1 show that it took 2 hours to convert only 10% of p-tert-butyl toluene to the desired ester, p-tert-butyl benzylacetate.

EXAMPLE II

This example illustrates the inventive catalyst, its preparation, and its activity.

The runs were carried out in a reactor containing acetic acid (2.667 moles). Palladium acetate (0.005 moles), charcoal (12 g), potassium acetate (0.367 moles), and potassium persulfate (0.059 moles) were added to the reactor. Following a thorough mixing, the suspension was heated to and held at 100° C. for 30 minutes.

After the suspension was heated, an extra amount of potassium acetate (0.184 moles) and stannous acetate (0.021 moles) were added to the heated suspension to form a catalyst suspension. The suspension was further mixed briefly to ensure a uniform mixture of the catalyst.

p-Tert-butyltoluene (0.101 moles) was then added to the catalyst solution followed by heating the reaction mixture at 100° C. for a period of time shown in Table 2. At time indicated in the Table, an aliquot of the reaction mixture was withdrawn for analysis of p-tert-butyl benzylacetate with a liquid chromatography, as described in Example I. The results are shown in Table 2.

TABLE 2

| | Oxidation of p-Tert-butyltoluene Catalyzed by Pd(OAc)$_2$/K$_2$S$_2$O$_8$/KOAc/Sn(OAc)$_2$, the Inventive Catalyst | | | |
|---|---|---|---|---|
| Run | Reaction Time (h) | Conversion (%) | Product | % of Product in Product Mixture |
| 3 | 1 | 75 | p-t-butyl benzylacetate | 75 |
| 4 | 2 | 96 | p-t-butyl benzylacetate | 96 |

The results shown in Table 2 clearly demonstrate that the inventive catalyst provides a benzylic oxidation of an alkylaromatic with a much higher conversion rate and product purity when compared to the results of the reference catalyst shown in Example I. For example, the oxidation is practically over within one hour whereas the reference catalyst requires at least 9 hours to achieve an 80% conversion (See also J. Org. Chem. 33:4125, Table II, 1968)

The oxidized product in this example and other examples were further characterized by other instrumental analyses, nuclear magnetic resonance analysis, GC-Mass spectrometric analysis, and elemental analysis. All analyses agreed with each other that the oxidized product of p-tert-butyl toluene was p-tert-butylacetate. Elemental analysis of the product also revealed that there was no sulfur present indicating that potassium persulfate is not a reactant incorporating its sulfur into the product.

EXAMPLE III

This example illustrates that the catalyst, if all components are mixed together at once, dramatically reduces its catalytic activity.

The runs were carried out the same as those described in Example II with the exception that all potassium acetate (total 0.551 moles) and stannous acetate were added with other catalyst components in the beginning followed by heating to and holding at 100° C. for 30 minutes. The results of the oxidation of p-tert-butyltoluene are shown in Table 3.

TABLE 3

| | Oxidation of p-Tert-butyl Toluene Catalyzed by One Stage-Prepared Pd(OAc)$_2$/KOAc/K$_2$S$_2$O$_8$/Sn(OAc)$_2$ | | | |
|---|---|---|---|---|
| Run | Reaction Time (h) | Conversion (%) | Product | % of Product in Product Mixture |
| 5 | 1 | 0.6 | p-t-butyl benzylacetate | 0.6 |
| 6 | 2 | 1.2 | p-t-butyl benzylacetate | 1.2 |

The results shown in Table 3 clearly indicate that, without heating the Pd(OAc)$_2$/K$_2$S$_2$O$_8$/KOAc mixture first, followed by addition of stannous acetate and extra potassium acetate, the catalyst has very low activity, when compared to the results shown in Table 2. For example, there was little or no reaction within the first hour if all catalyst components were heated at the same time. The results further demonstrate the importance of the order of catalyst preparation because very low catalyst activity was obtained if the two stage preparation process illustrated in Example II was not practiced.

While this invention has been described in detail for the purpose of illustration, it is not to be construed or limited thereby but is intended to cover all changes and modifications within the spirit and scope thereof.

That which is claimed is:

1. A process for oxidizing an alkylaromatic having a benzylic hydrogen to its corresponding oxidized product selected from the group consisting of carboxylic acids, aldehydes, alcohols and esters comprising contacting said alkylaromatic in the presence of an oxygen-containing fluid in a reaction medium with a catalyst comprising a palladium salt, a metal persulfate, a third metal salt having a general formula of MX wherein M is an alkali or alkaline earth metal and X is selected from the group consisting of carboxylate, acrylate, sulfate, nitrate, phosphate, and halide and a tin salt, in a carboxylic acid under conditions sufficient to oxidize said benzylic hydrogen of said alkylaromatic.

2. A process according to claim 1 wherein said alkylaromatic has a general formula of

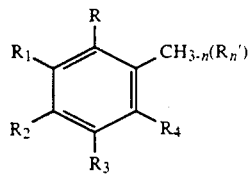

wherein R, R$_1$, R$_2$, R$_3$, and R$_4$ are hydrogen atoms, or same or different alkyl, alkoxyl, or cycloalkyl groups; and R' is a saturated alkyl or cycloalkyl group having 1 to 9 carbon atoms; and n is 0, 1, or 2.

3. A process according to claim 2 wherein said alkylaromatic is selected from the group consisting of toluene, p-xylene, m-xylene, o-xylene, p-tert-butyltoluene, p-octyltoluene, p-cresol, and p-cyclohexyltoluene.

4. A process according to claim 3 wherein said alkylaromatic is p-tert-butyl toluene.

5. A process according to claim 1 wherein;
said palladium salt is selected from the group consisting of palladium acrylate, palladium acetate, palladium propionate, palladium butyrate, palladium hexanoate, palladium cyclohexanoate, palladium chloride, and palladium nitrate;
said metal persulfate is selected from the group consisting of lithium persulfate, sodium persulfate, potassium persulfate, magnesium persulfate, and calcium persulfate;
said third metal salt is selected from the group consisting of lithium acetate, sodium acetate, potassium acetate, potassium propionate, potassium butyrate, potassium acrylate, potassium sulfate, potassium phosphate and potassium chloride;
said tin salt is selected from the group consisting of stannous acetate, stannous propionate, stannous butyrate, stannous laurate, stannous oleate, stannous benzoate, stannous gluconate, stannous naphthenate, stannous chloride, and stannous nitrate; and
said carboxylic acid is selected from the group consisting of formic acid, acetic acid, propionic acid, butyric acid, octanoic acid, lauric acid, stearic acid, and chloroacetic acid.

6. A process according to claim 5 wherein said palladium salt is palladium acetate, said metal persulfate is potassium persulfate, said third metal salt is potassium acetate and said carboxylic acid is acetic acid.

7. A process according to claim 1 wherein said reaction medium is a carboxylic acid.

8. A process according to claim 7 wherein said carboxylic acid is selected from the group consisting of formic acid, acetic acid, propionic acid, butyric acid, octanoic acid, lauric acid, stearic acid, and chloroacetic acid.

9. A process according to claim 8, wherein said carboxylic acid is acetic acid.

10. A process according to claim 1 wherein said oxidized product is p-tert-butyl benzylacetate.

11. A process according to claim 1 wherein said period of time is about 1 minute to about 20 hours.

12. A process according to claim 11 wherein said period of time is about 5 minutes to about 10 hours.

13. A process according to claim 1 wherein:
said alkylaromatic is selected from the group consisting of toluene, p-xylene, o-xylene, m-xylene, p-tert-butyl toluene, p-octyl toluene, p-cresol, and p-cyclohexyl toluene;
said palladium salt is selected from the group consisting of palladium acrylate, palladium acetate, palladium propionate, palladium butyrate, palladium hexanoate, palladium cyclohexanoate, palladium chloride, and palladium nitrate;
said metal persulfate is selected from the group consisting of lithium persulfate, sodium persulfate, potassium persulfate, magnesium persulfate, and calcium persulfate;
said third metal salt is selected from the group consisting of lithium acetate, sodium acetate, potassium acetate, potassium propionate, potassium butyrate, potassium acrylate, potassium sulfate, potassium phosphate and potassium chloride;
said tin salt is selected from the group consisting of stannous acetate, stannous propionate, stannous butyrate, stannous laurate, stannous oleate, stannous benzoate, stannous gluconate, stannous naphthenate, stannous chloride, and stannous nitrate;
said carboxylic acid is a saturated aliphatic carboxylic acid selected from the group consisting of formic acid, acetic acid, propionic acid, butyric acid, octanoic acid, lauric acid, stearic acid, and chloroacetic acid;
said reaction medium is a carboxylic acid;
said oxidized product is selected from the group consisting of carboxylic acid, aldehyde, alcohol, and ester; and
said period of time is about 1 minute to about 20 hours.

14. A process according to claim 13 wherein said alkylaromatic is p-tert-butyl toluene, said palladium salt is palladium acetate, said second metal salt is potassium acetate, said metal persulfate is potassium persulfate, said tin salt is stannous acetate, said reaction medium is acetic acid, said oxidized products is p-tert-butyl benzylacetate, and said period of time is about 5 minutes to about 10 hours.

* * * * *